(12) United States Patent
Brackett et al.

(10) Patent No.: US 8,121,866 B2
(45) Date of Patent: Feb. 21, 2012

(54) SYSTEM AND METHOD FOR DISPLAYING PEDIATRIC CARDIOLOGY Z-SCORES

(75) Inventors: C. Cameron Brackett, Overland Park, KS (US); Craig A. Gaskill, Kansas City, MO (US); Michael Harkavy, Kansas City, MO (US)

(73) Assignee: Cerner Innovation, Inc., Overland Park, KS (US)

( * ) Notice: Subject to any disclaimer, the term of this patent is extended or adjusted under 35 U.S.C. 154(b) by 1225 days.

(21) Appl. No.: 11/771,676

(22) Filed: Jun. 29, 2007

(65) Prior Publication Data

US 2008/0059243 A1    Mar. 6, 2008

Related U.S. Application Data

(60) Provisional application No. 60/806,336, filed on Jun. 30, 2006.

(51) Int. Cl.
G06Q 50/00     (2006.01)
G06Q 10/00     (2006.01)

(52) U.S. Cl. .......................................................... 705/3

(58) Field of Classification Search ................... 705/2–3
See application file for complete search history.

(56) References Cited

U.S. PATENT DOCUMENTS

| | | | |
|---|---|---|---|
| 2003/0073884 A1* | 4/2003 | Goldberg | 600/300 |
| 2003/0233250 A1* | 12/2003 | Joffe et al. | 705/2 |
| 2006/0085249 A1* | 4/2006 | Diaz et al. | 705/11 |
| 2006/0287891 A1* | 12/2006 | Grasso et al. | 705/3 |

OTHER PUBLICATIONS

C. Schneider, et al. Development of Z-scores for fetal cardiac dimensions from echocardiography (2005), Ultrasound Obstet Gynecol 26: 566-605.*

SAS/Insight Software, Fit Regression Models. <http://web.archive.org/web/20050301071441/http://support.sas.com/md/app/da/insight/in_fit.html>.*

Telemedicine Business Week. University of Hong Kong, People's Republic of China; Research from the People's Republic of China, India, and United States in Cardiology Provides New Insights. Atlanta: Jul. 19, 2006, p. 150.*

* cited by examiner

*Primary Examiner* — Sheetal R Rangrej
(74) *Attorney, Agent, or Firm* — Shook Hardy & Bacon L.L.P.

(57) ABSTRACT

A method for simultaneously displaying a procedure documentation form and pediatric cardiology z-scores for a patient is provided. Documentation data for the patient is received and a database including pediatric cardiology data for a computerized z-score graph appropriate for a patient is accessed. The pediatric cardiology data and documentation data are utilized to calculate one or more z-scores for the patient. The one or more z-scores are displayed on a computerized graph simultaneously with the procedure documentation form.

20 Claims, 7 Drawing Sheets

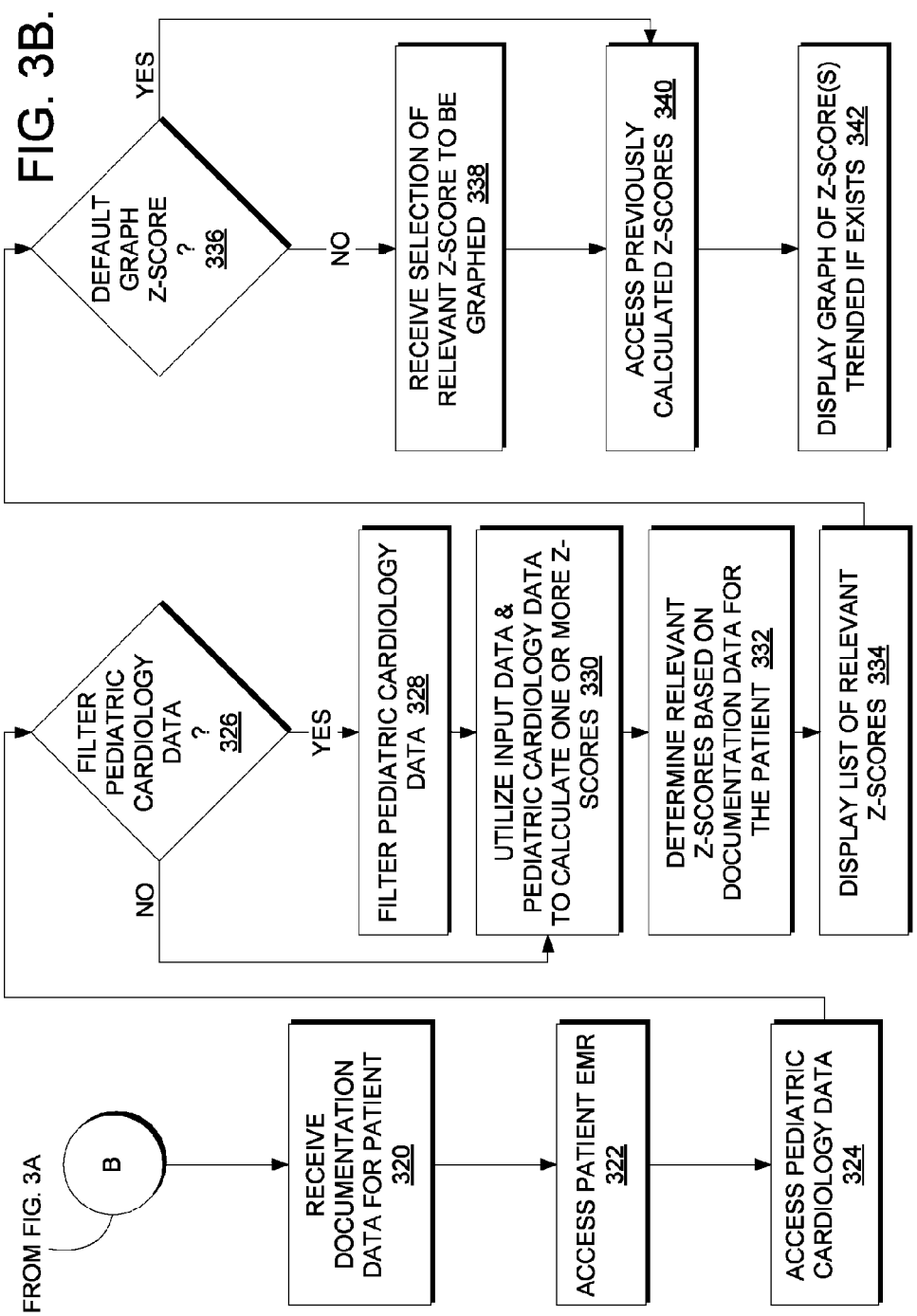

SYSTEM AND METHOD FOR DISPLAYING PEDIATRIC CARDIOLOGY Z-SCORES

CROSS-REFERENCE TO RELATED APPLICATIONS

This application is a non-provisional of and claims the benefit of priority of U.S. Provisional Application No. 60/806,336 filed on Jun. 30, 2006.

STATEMENT REGARDING FEDERALLY SPONSORED RESEARCH OR DEVELOPMENT

Not applicable.

BACKGROUND

In pediatric cardiology, z-scores are commonly used to determine how a patient's heart measures in relation to a population mean. Z-scores are a measure of a distance of a patient's measurements in standard deviations of a sample from a mean. Pediatric cardiologists create many z-scores around the heart and plot those values against a mean of the population to determine abnormalities. Exemplary z-scores include: End Diastolic Diameter (EDD) vs. Time, Aortic Annulus Diameter (AAD) vs. Body Surface Area (BSA), Fractional Shortening vs. Time and Wall Thickness vs. Time. Graphs that plot the patient's measurements in the form of z-scores against a mean of the population are used to diagnose the patient.

Currently, most pediatric cardiology z-scores are graphed manually. Integrated computerized graphing systems do not provide the access to patient data, such as a patient's electronic medical record (EMR), when graphing patient z-scores. Furthermore, the electronic z-score graphs do not allow the patient's cardiology z-score data to be filtered according to user preference. These z-score graphs only display data for one particular procedure and do not have the capability to display more than one z-score graph side by side, e.g. EDD vs. Time and ADD vs. BSA simultaneously. Nor do the electronic z-score graphs have the capability to display current and previously calculated z-scores for a patient. These electronic z-score graphs also do not allow for a patient's z-score graph to be displayed at the same time a user is documenting a current procedure.

SUMMARY OF THE INVENTION

In one aspect, the present invention relates to a method in a computerized health care environment for simultaneously displaying a patient's current procedure documentation and pediatric cardiology z-scores. The method comprises receiving documentation data for a patient, accessing pediatric cardiology data and utilizing the patient data and the pediatric cardiology data to calculate one or more pediatric cardiology z-scores. The method further comprises displaying one or more pediatric cardiology z-scores on a computerized graph and displaying a documentation form simultaneously with one or more pediatric cardiology z-scores on a computerized graph.

In another embodiment, the present invention relates to a method in computerized health care environment for simultaneously displaying a patient's current procedure documentation and pediatric cardiology z-scores. The method comprises receiving documentation data for a patient, accessing pediatric cardiology data and utilizing the patient data and the pediatric cardiology data to calculate a pediatric cardiology z-score. The method further comprises accessing a previously calculated pediatric cardiology z-score and displaying the calculated pediatric cardiology z-score and the previously calculated pediatric cardiology z-score together on a computerized graph simultaneously with a documentation form.

In another embodiment, the present invention relates to a method in a computerized health care environment for simultaneously displaying a patient's current procedure documentation and pediatric cardiology z-scores. The method comprises accessing one or more previously calculated pediatric cardiology z-scores for a patient and displaying one or more previously calculated pediatric cardiology z-scores on a computerized graph. The method further comprises displaying a documentation form simultaneously with one or more pediatric cardiology z-scores on the computerized graph.

In yet another embodiment, a user interface embodied on at least one computer readable medium is described. The user interface simultaneously displays a procedure documentation form for a pediatric cardiology patient and calculated z-scores. The user interface comprises a first display area configured to display a documentation form for a patient, the documentation form for input of pediatric cardiology data for the patient and a second display area configured to display a graph comprising one or more z-scores calculated utilizing the pediatric cardiology data for the patient.

BRIEF DESCRIPTION OF THE SEVERAL VIEWS OF THE DRAWINGS

The present invention is described in detail below with reference to the attached drawing figures, wherein:

FIG. 3B is a flow diagram of a method for receiving documentation data, calculating z-scores and displaying a graph of trended relevant z-scores in accordance with an embodiment of the present invention;

FIG. 4 is a screen displaying a procedure work list in accordance with an embodiment of the present invention;

FIG. 5 is an exemplary interactive display for documenting current procedure data in accordance with an embodiment of the present invention;

FIG. 7 is a screen displaying a procedure documentation form and a graph of the calculated z-scores in accordance with an embodiment of the present invention

DETAILED DESCRIPTION OF THE INVENTION

Figure 1:
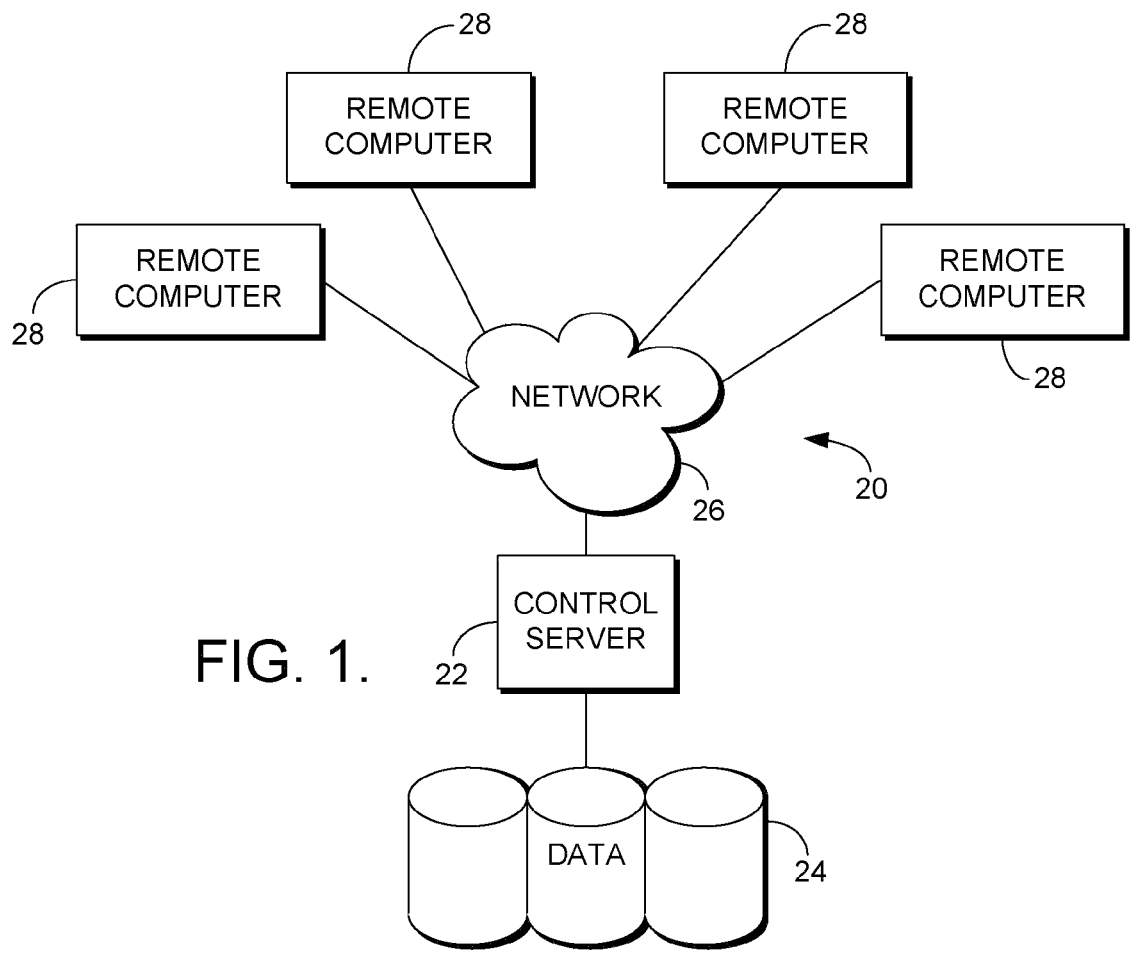
FIG. 1 is a block diagram of a computing system environment suitable for use in implementing the present invention.

With reference to FIG. 1, an exemplary medical information system for implementing the invention includes a general purpose-computing device in the form of server 22. Components of server 22 may include, but are not limited to, a processing unit, internal system memory, and a suitable system bus for coupling various system components, including database cluster 24 to the control server 22. The system bus may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Server 22 typically includes therein or has access to a variety of computer readable media, for instance, database cluster 24. Computer readable media can be any available media that can be accessed by server 22, and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information, such as computer readable instructions, data structures, program modules or other data. Computer storage media includes, but is not limited to, RAM, ROM, EEPROM, flash memory or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by server 22. Communication media typically embodies computer readable instructions, data structures, program modules, or other data in a modulated data signal, such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media, such as a wired network or direct-wired connection, and wireless media such as acoustic, RF, infrared and other wireless media. Combinations of any of the above should also be included within the scope of computer readable media.

The computer storage media, including database cluster 24, discussed above and illustrated in FIG. 1, provide storage of computer readable instructions, data structures, program modules, and other data for server 22.

Server 22 may operate in a computer network 26 using logical connections to one or more remote computers 28. Remote computers 28 can be located at a variety of locations in a medical or research environment, for example, but not limited to, clinical laboratories, hospitals, other inpatient settings, a clinician's office, ambulatory settings, medical billing and financial offices, hospital administration, veterinary environment and home health care environment. Clinicians include, but are not limited to, the treating physician, specialists such as surgeons, radiologists and cardiologists, emergency medical technologists, physician's assistants, nurse practitioners, nurses, nurse's aides, pharmacists, dieticians, microbiologists, laboratory experts, genetic counselors, researchers, veterinarians and the like. The remote computers may also be physically located in non-traditional medical care environments so that the entire health care community is capable of integration on the network. Remote computers 28 may be a personal computer, server, router, a network PC, a peer device, other common network node or the like, and may include some or all of the elements described above relative to server 22. Computer network 26 may be a local area network (LAN) and/or a wide area network (WAN), but may also include other networks. Such networking environments are commonplace in offices, enterprise-wide computer networks, intranets and the Internet. When utilized in a WAN networking environment, server 22 may include a modem or other means for establishing communications over the WAN, such as the Internet. In a networked environment, program modules or portions thereof may be stored in server 22, or database cluster 24, or on any of the remote computers 28. For example, and not limitation, various application programs may reside on the memory associated with any one or all of remote computers 28. It will be appreciated that the network connections shown are exemplary and other means of establishing a communications link between the computers may be used.

A user may enter commands and information into server 22 or convey the commands and information to the server 22 via remote computers 28 through input devices, such as keyboards, pointing devices, commonly referred to as a mouse, trackball, or touch pad. Other input devices may include a microphone, satellite dish, scanner, or the like. Server 22 and/or remote computers 28 may have any sort of display device, for instance, a monitor. In addition to a monitor, server 22 and/or computers 28 may also include other peripheral output devices, such as speakers and printers.

Although many other internal components of server 22 and computers 28 are not shown, those of ordinary skill in the art will appreciate that such components and their interconnection are well known. Accordingly, additional details concerning the internal construction of server 22 and computer 28 need not be disclosed in connection with the present invention.

Although the method and system are described as being implemented in a WINDOWS operating system operating in conjunction with an Internet-based system, one skilled in the art would recognize that the method and system can be implemented in any system.

Figure 2:
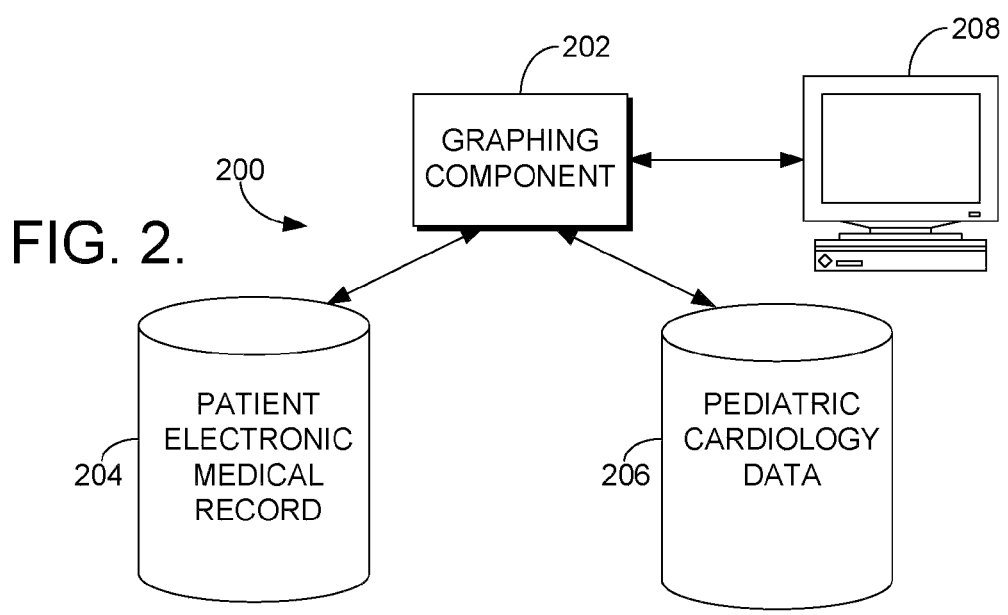
FIG. 2 is a block diagram of an exemplary system for use in implementing embodiments of the present invention.

Referring next to FIG. 2, a block diagram of an exemplary system for use in implementing one or more embodiments of the present invention is shown. The system 200 comprises a graphing component 202 which is in communication with computerized databases 204 and 206. Graphing component 202 may be in communication with or located on a remote computer 208 to be used by a user. Graphing component 202 accesses pediatric cardiology data from database 206 to obtain graph definitions, statistical information and historical records and measurements for previously treated patients.

Graph definitions include the type of data that is plotted for a z-score, such as EDD vs. Time, AAD vs. BSA, Fractional Shortening vs. Time and Wall Thickness vs. Time. In other words, fractional shortening measurements will be plotted against time and the Aortic Annulus Diameter will be plotted against Body Surface Area. The graph definitions include the age ranges, genders and race of the patients for which the graph applies, as well as the source of the chart and actual physical characteristics of the graph. Statistical and historical information for each type of z-score for several age ranges, gender and race is also stored in pediatric cardiology data 206. Historical records include previous graph definitions, trends, reference curves and data, and calculated z-scores and measurements for previously treated patients.

Figure 6:
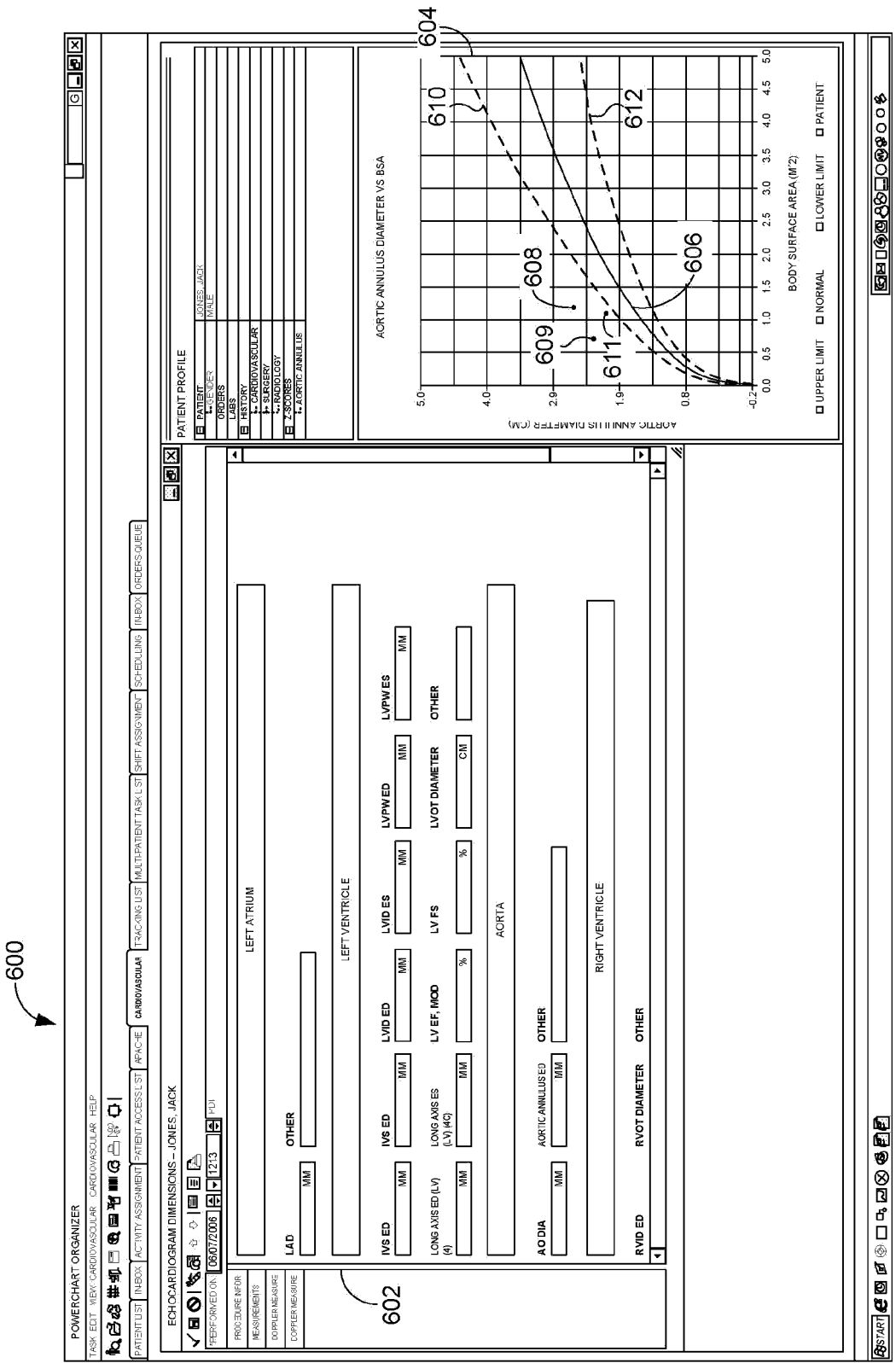
FIG. 6 is a screen displaying a current procedure documentation form and a graph of previously calculated z-scores in accordance with an embodiment of the present invention.

The reference curves are a series of points identified with a particular z-score for a set of previously treated patients. For example, a curve representing "normal" or median z-scores for a population of previously treated patients as illustrated in FIG. 6 at 606 may be stored as several X and Y value pairs. The set of previously treated patients may be boys ages two to five years old or may be for all pediatric cardiology patients. The graphing component 202 plots the X and Y value pairs on the graph and connects them to create a reference curve. In FIG. 6, the "X" value is Body Surface Area and the "Y" value is the Aortic Annulus Diameter. The reference curves are drawn on a graph by plotting each of the data points and connecting them with a smooth curve.

Database 204 includes patient data. In one embodiment, patient data is stored in a patient's electronic medical record (EMR). A patient EMR may include patient data such as the patient's age, gender, weight, race, date recorded, recorded problems or diagnoses, procedures performed, previously calculated z-scores for the patient, measurements, and a variety of other patient data.

Figure 3A:
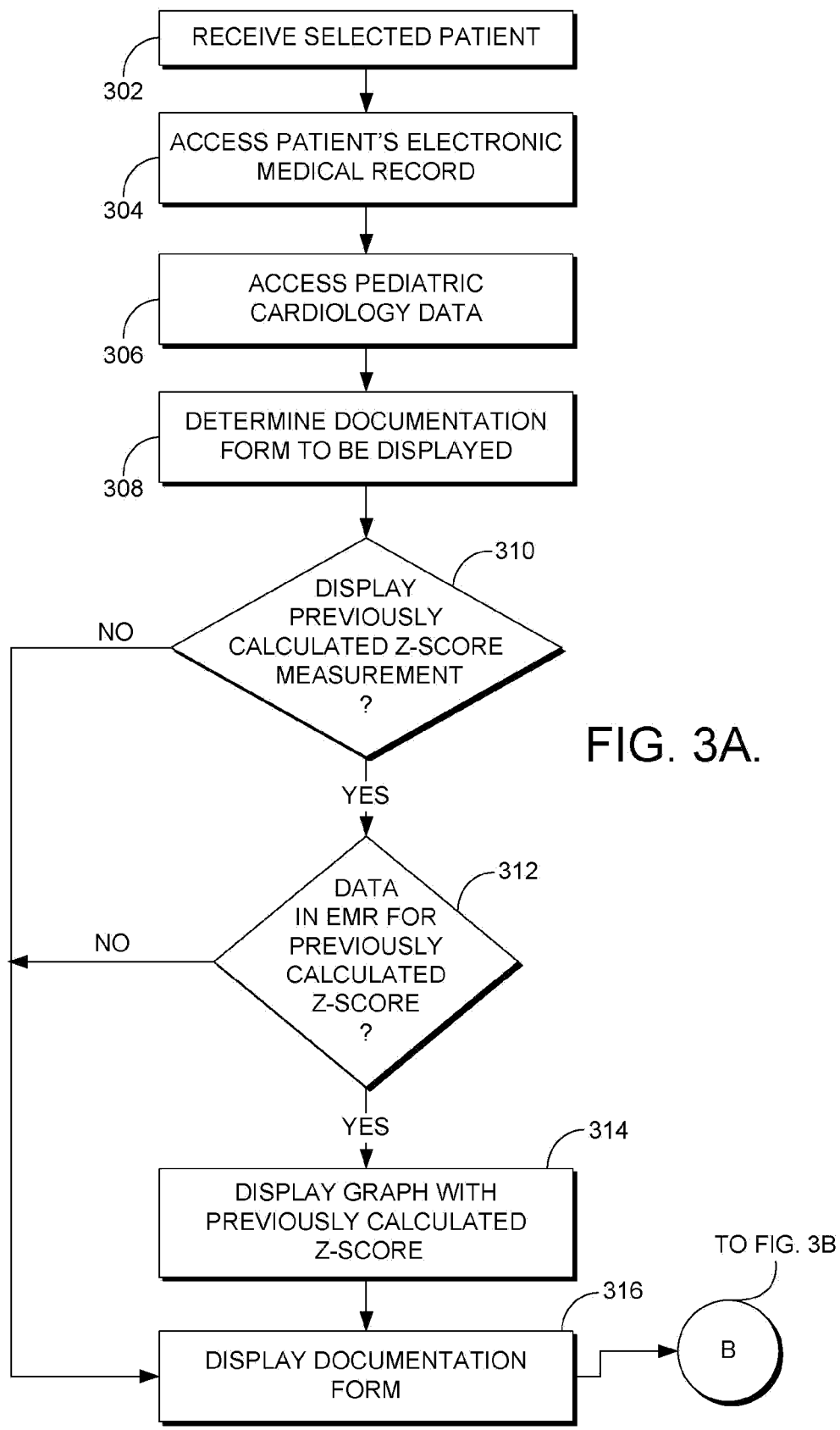
FIG. 3A is a flow diagram of a method for displaying previously calculated z-score measurements and documentation form for a patient in accordance with an embodiment of the present invention.
Figure 4:
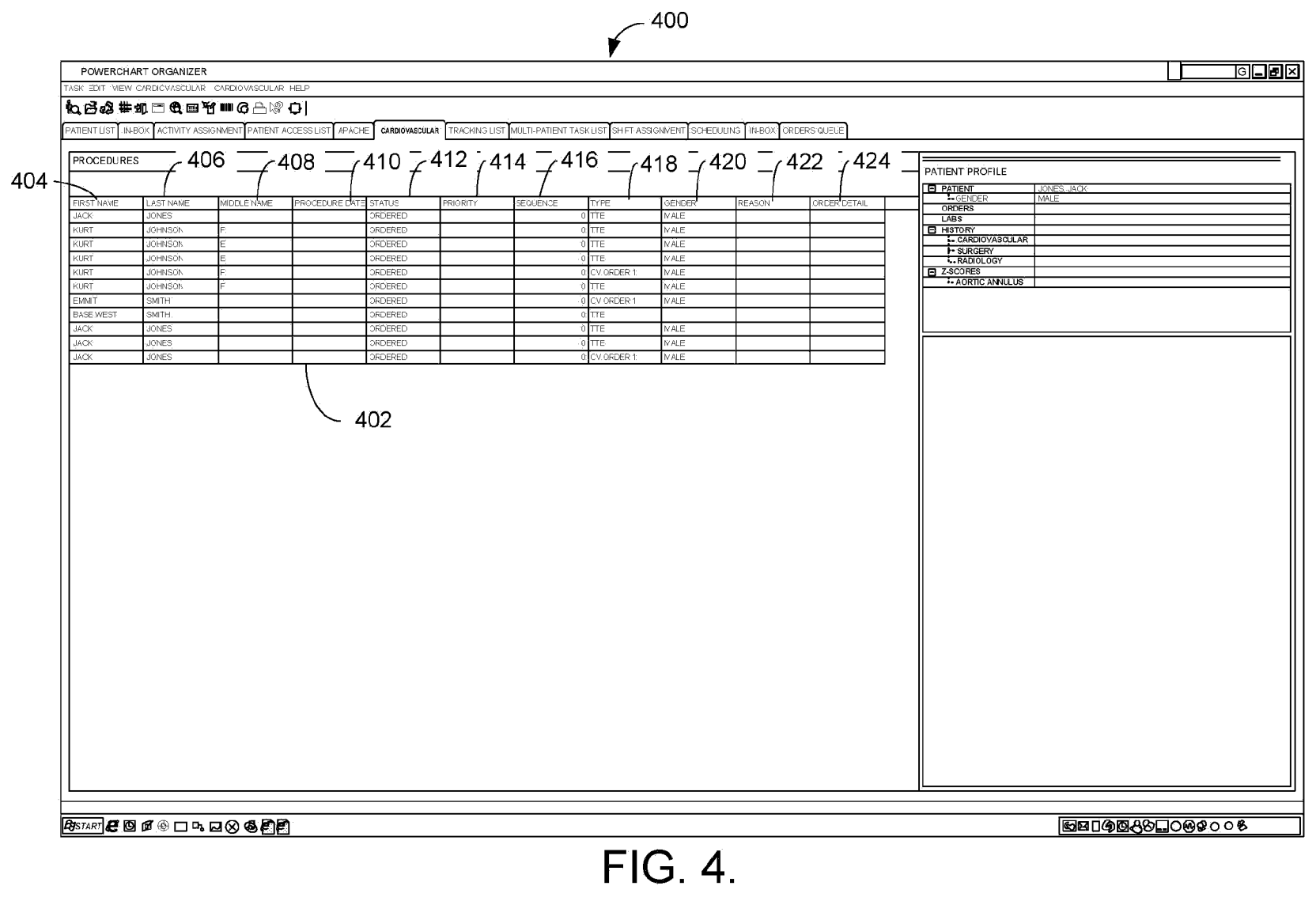

With reference to FIG. 3A, a method for displaying both previously calculated z-scores and patient data documentation form is shown. At step 302, the appropriate patient is selected. With reference to FIG. 4, an exemplary task list screen 400 is displayed. A unified healthcare architecture such as Cerner Millennium by Cerner Corporation of Kansas City, Mo. may be utilized. The patient cardiovascular task list 400 includes one or more patients and task items to be completed for each of the one or more patients. In one embodiment, a patient is selected by a user from a patient list 400. The user may be a health care provider such as a nurse, doctor or other health care worker. Patient list 402 includes information regarding the patients such as first name 404, last name 406, middle name 408, procedure date 410, status 412, priority 414, sequence 416, type 418, gender 420, reason 422, and order details 424.

Referring again to FIG. 3A, at step 304, the patient's EMR is accessed. The patient's EMR may include patient data such as the patient's age, gender, weight, race, date recorded, recorded problems or diagnoses, previously calculated z-scores, measurements, orders and any other information that has been documented for the patient along with when and by whom the documentations were made.

At step 306, the pediatric cardiology data is accessed. Pediatric cardiology data includes graph definitions, statistical information and historical records for a patient population. Graph definitions include unique characteristics of a type of z-score such as End Diastolic Diameters (EDD) vs. Time, Aortic Annulus Diameter (AAD) vs. Body Surface Area (BSA), Fractional Shortening vs. Time and Wall Thickness vs. Time. The graph definitions include the set of patients by age ranges, genders and race of the patients for which the graph applies, as well as the source of the chart and actual physical characteristics of the graph. Historical records include previous graph definitions, references curves, trends, and statistical information for graphs that have changed, and patient historical records.

At step 308, the documentation form to be displayed is determined. The documentation form allows a user to enter cardiology measurements for the patient. In one embodiment, the documentation form will be automatically displayed once a patient is selected based on default preferences of the user or system. At step 310, a determination is made as to whether one or more previously calculated z-score measurements are to be displayed. This may be a default in the system or based on user preferences. If previously calculated z-score measurements are not to be displayed, then at step 316 a patient cardiology documentation form is displayed.

Referring to FIG. 3A, if at step 310, one or more previously calculated z-score measurement are to be displayed, at step 312, a determination is made as to whether one or more previously calculated z-scores exist in the patient's EMR. If one or more previously calculated z-scores do not exist, at step 316 a cardiology documentation form is displayed. The documentation form is displayed without a graph of previously calculated z-scores as illustrated in documentation form 500 of FIG. 5. If previously calculated z-scores exist for a patient, then at step 314 a graph with previously calculated z-scores will be displayed alongside the default documentation form at step 316. The documentation form is displayed along side a graph containing previously calculated z-scores as illustrated in documentation form 600 of FIG. 6.

Figure 5:
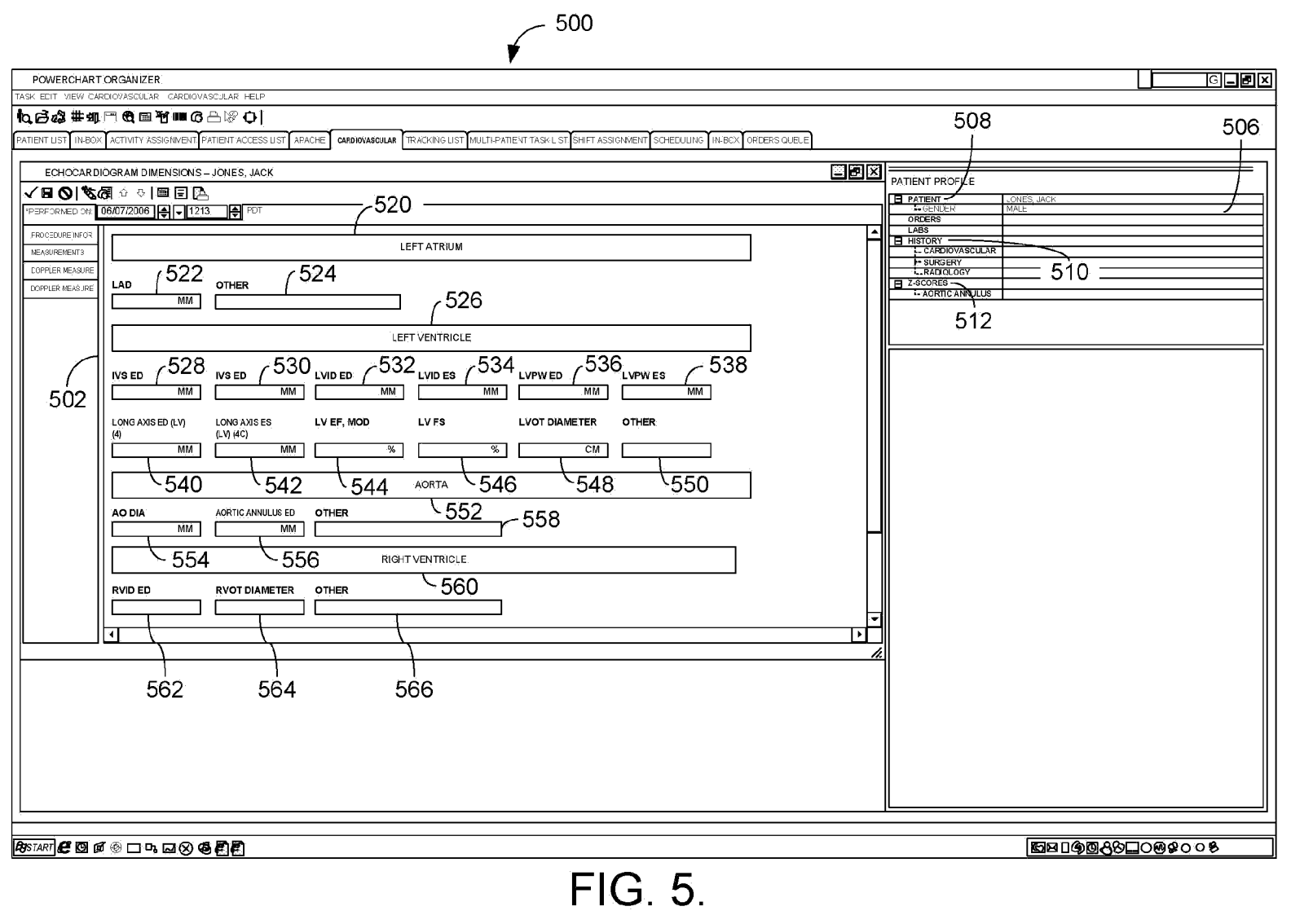

By way of example, and not by limitation, with reference to FIG. 5, an exemplary interactive documentation form 500 without a graph of previously calculated z-scores for the patient is displayed. The exemplary documentation form 500 includes documentation fields 502 where the user enters cardiology measurements for the patient. The documentation form for the Left Atrium 520 may include fields such as Left Anterior Descending Artery (LAD) 522 and Other 524. The documentation form for the Left Ventricle 526 may include fields such as Interventricular Septum at End-Diastolic (IVS ED) 528, Interventricular Septum at End-Systolic (IVS ES) 530, Left Ventricular Internal Dimensions at End-Diastolic (LVID ED) 532, Left Ventricular Internal Dimensions at End-Systolic (LVID ES) 534, Left Ventricular Posterior Wall at End-Diastolic (LVPW ED) 536, Left Posterior Wall at End-Systolic (LVPW ES) 538, Long Axis at End-Diastolic 540, Long Axis at End-Systolic 542, Left Ventricular Ejection Fraction, Moderate (LVEF, MOD) 544, Left Ventricular Fractional Shortening (LVFS) 546, Left Ventricular Outflow Tract (LVOT) Diameter 548 and Other 550. The documentation form for the Aorta 552 may include fields such as Aortic Diameter 554, Aortic Annulus at End-Diastolic 556 and Other 558. The documentation form for the Right Ventricle 560 may include fields such as Right Ventricular Internal Dimensions at End-Diastolic (RVID ED) 562 and Right Ventricular Outflow Tract (RVOT) Diameter 564 and Other 566.

By way of example, the patient's aortic diameter will be input in field 554. In one embodiment, documentation form 500 may also include a patient profile 506 which gives the user access to various information pertaining to the selected patient. The information provided in patient profile 506 can be accessed by selecting the appropriate term associated with the information desired. In one embodiment, the patient profile can provide the user with access to other patient data 508, procedure history 510 and calculated z-scores 512.

By way of example, and not by limitation, with reference to FIG. 6, an exemplary interactive documentation form 600 and graph 604 of previously calculated z-scores for the patient are displayed. The documentation form 602 is displayed simultaneously with graph 604 displaying previously calculated z-scores 608, 609, and 611 for the patient. Reference curves 606, 610, and 612 are displayed on the graph 604. Reference curves 606, 610, and 612 allow the user to determine where the patient's z-score 608 falls in relation to z-scores of similar patients (e.g., a set of patients or similar age, gender and race.) For example, reference curve 606 represents the median z-score reference curve, the population set reference curve 610 represents the upper end of z-scores and reference curve 612 represents the lower end of z-scores. In another embodiment, the user has the ability to select on a point on the graph, such as z-score 608, and pull up the full report and images associated with that z-score.

Referring next to FIG. 3B, a method for receiving documentation data, calculating z-scores and displaying a graph of relevant z-scores is shown. At step 320, documentation data for a patient is received. The documentation data may include patient cardiology measurements and information entered into a documentation form. At step 322, the patient's EMR is accessed for patient data. At step 324, pediatric cardiology data is accessed from a database or table. At step 326, a determination is made as to whether or not to filter the cardiology data. In one embodiment, a user may want limit the pediatric cardiology data utilized to calculate a z-score for the patient to the data that the user determines to be relevant.

In one embodiment, the user may limit the pediatric cardiology data to be filtered to only the data that is related to the current procedure or based on patient demographics. In another embodiment, the data is automatically filtered based on default criteria such as patient demographics obtained from patient data. If cardiology data is to be filtered, then at step 328, the pediatric cardiology data is filtered accordingly. At step 330, the documentation data received and the pediatric cardiology data (filtered or unfiltered) is used to calculate one or more z-scores.

At step 332, the relevant z-scores, based on documentation data for the patient, are determined. In one embodiment, a relevant z-score is a z-score that is directly associated with one or more measurements for the given procedure. In another embodiment, a relevant z-score is a z-score that is not related to a measurement for the procedure, but has conditionality parameters for presentation. An example of this would be a z-score that is outside a pre-defined threshold. The relevant z-score may also be a combination of direct association, indirect association and conditionality parameters. The relevant parameters may be defaults in the system, entered by a user or defaults based on the user.

Figure 7:
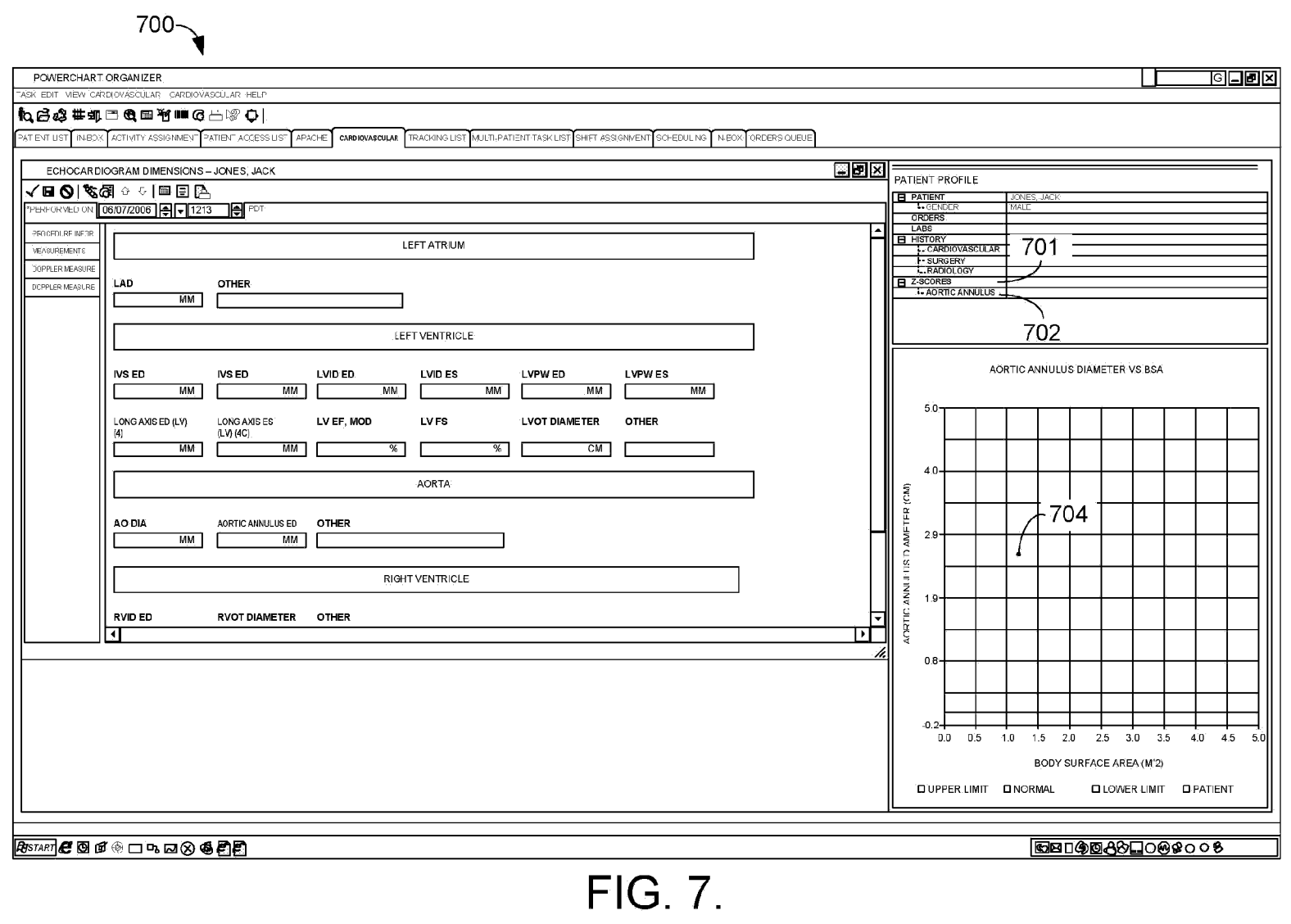

At step 334, the list of relevant z-scores for the patient is displayed. An illustrative example of a list of relevant z-scores 701 is shown in FIG. 7. In this example, the relevant z-score listed for the patient is the Aortic Annulus 702 z-score. In one embodiment, the relevant z-scores may be highlighted in order to differentiate them from the non-relevant z-scores.

Referring again to FIG. 3B, at step 336, it is determined whether there is a default type of z-score that should be graphed. For example, a pre-defined or default type of z-score may be graphed automatically for a patient. For example, the system may default to automatically display the Aortic Annulus Diameter v. BSA z-score.

If there is a default z-score to be graphed, at step 340, the current and previously calculated z-scores for the default type of z-score for the patient are accessed and plotted on the graph. For example, if the default z-score to graph is the AAD v. BSA z-score, the current AAD v. BSA z-score and the previously calculated AAD v. BSA z-scores calculated for the patient are accessed to be plotted on the graph. If, at step 336, it is determined that there is no default z-score to graph, the user selects a z-score from the list of relevant z-scores. For example, in FIG. 7, the Aortic Annulus z-score 702 may be selected to graph.

Referring again to FIG. 3B, at step 338, a selection of relevant z-scores to be graphed is received. At step 340, the current and previously calculated z-scores for the type of z-score selected for the patient are accessed. At step 342, a graph of the selected z-scores for the patient is displayed.

If there are current and previously calculated z-scores for the same z-score type, each z-score is plotted on the graph. Referring to FIG. 6, current and previously calculated z-scores 608, 609, and 611 for a patient are displayed on a graph. In one embodiment, a hue differentiation can be used to show time progression of the z-scores for the patient. For example, the darker the point, the more recent the calculation of the z-score for the patient. With reference to FIG. 7, an exemplary graph displaying only the current calculated z-score 704 for a patient is shown.

In another embodiment, the present invention relates to a system in a computerized health care environment for simultaneously displaying a patient's current procedure documentation and pediatric cardiology z-scores. The system comprises a first receiving component receiving documentation data for a patient, an accessing component accessing pediatric cardiology data and utilizing the patient data and the pediatric cardiology data to calculate one or more pediatric cardiology z-scores. The system further comprises a displaying component displaying one or more pediatric cardiology z-scores on a computerized graph and displaying a documentation form simultaneously with one or more pediatric cardiology z-scores on a computerized graph.

In another embodiment, the present invention relates to a system in a computerized health care environment for simultaneously displaying a patient's current procedure documentation and pediatric cardiology z-scores. The system comprises a receiving component receiving documentation data for a patient, a first accessing component accessing pediatric cardiology data and utilizing the patient data and the pediatric cardiology data to calculate a pediatric cardiology z-score. The system further comprises a second accessing component accessing a previously calculated pediatric cardiology z-score and a displaying component displaying the calculated pediatric cardiology z-score and the previously calculated pediatric cardiology z-score together on a computerized graph simultaneously with a documentation form.

In another embodiment, the present invention relates to a system in a computerized health care environment for simultaneously displaying a patient's current procedure documentation and pediatric cardiology z-scores. The system comprises an accessing component accessing one or more previously calculated pediatric cardiology z-scores for a patient and first displaying component displaying one or more previously calculated pediatric cardiology z-scores on a computerized graph. The system further comprises second displaying component displaying a documentation form simultaneously with one or more pediatric cardiology z-scores on the computerized graph.

The present invention has been described in relation to particular embodiments, which are intended in all respects to illustrate rather than restrict. Alternative embodiments will become apparent to those skilled in the art that do not depart from its scope. Many alternative embodiments exist, but are not included because of the nature of the invention. A skilled programmer may develop means for implementing the aforementioned improvements without departing from the scope of the present invention.

It will be understood that certain features and sub-combinations of utility may be employed without reference to features and sub-combinations and are contemplated within the scope of the claims. Furthermore, the steps performed need not be performed in the order described.

The invention claimed is:

1. Computer-readable storage media having embodied thereon computer-useable instructions that, when executed, implement a method in a computerized health care environment for simultaneously displaying pediatric cardiology z-scores for a patient and a documentation form for the entry of cardiology measurements, the method comprising:

retrieving data for the patient from an electronic medical record source, the data comprising previously calculated pediatric cardiology z-scores for the patient and at least one of age, gender, weight, race, recorded problems or diagnoses, procedures performed, or measurements for the patient;

displaying at least one of the previously calculated pediatric cardiology z-scores for the patient on a computerized graph simultaneously with the documentation form for the entry of cardiology measurements for the patient;

receiving cardiology measurements for the patient on the documentation form;

accessing pediatric cardiology data, pediatric cardiology data comprising at least one of pediatric cardiology z-score graph definitions, reference curves, and z-scores for previously treated patients;

utilizing the cardiology measurements for the patient and the pediatric cardiology data to calculate one or more current pediatric cardiology z-scores for the patient; and displaying one or more of the current pediatric cardiology z-scores on the computerized graph.

2. The computer-readable storage media of claim 1, wherein said pediatric cardiology z-scores are a measure of a distance of the patient's measurements in standard deviations of a sample from a mean.

3. The computer-readable storage media of claim 1, wherein the one or more z-scores displayed are associated with the cardiology measurements received.

4. The computer-readable storage media of claim 1, wherein the pediatric cardiology data reference curves are displayed simultaneously with current pediatric cardiology z-scores and previously calculated pediatric cardiology z-scores on the computerized graph.

5. The computer-readable storage media of claim 1, wherein the documentation form is automatically displayed.

6. The computer-readable storage media of claim 1, wherein the documentation form includes a patient profile.

7. The computer-readable storage media of claim 1, wherein the received cardiology measurements are filtered.

8. The computer-readable storage media of claim 7, wherein the filtered cardiology measurements are used to calculate the current pediatric cardiology z-score.

9. The computer-readable storage media of claim 8, wherein the current pediatric cardiology z-scores based on the filtered cardiology measurements are highlighted to distinguish them from the current pediatric cardiology z-scores based on the unfiltered cardiology measurements.

10. The computer-readable storage media of claim 1, wherein the previously calculated pediatric cardiology z-scores and the current pediatric cardiology z-scores are represented as points on the computerized graph, and further wherein a point on the computerized graph can be selected to display a full report on the cardiology measurements used in the calculation of the pediatric cardiology z-score at the point.

11. Computer-readable storage media having embodied thereon computer-useable instructions that, when executed, implement a method in a computerized health care environment for simultaneously displaying a documentation form for the entry of cardiology measurements and pediatric cardiology z-scores, the method comprising:

retrieving data for a patient from an electronic medical record source, the data comprising at least one previously calculated pediatric cardiology z-scores for the patient;

displaying the at least one previously calculated pediatric cardiology z-scores for the patient on a computerized graph simultaneously with the documentation form for the entry of cardiology measurements for the patient;

receiving cardiology measurements for the patient on the documentation form, the cardiology measurements comprising measurements associated with at least one of the left ventricle, right ventricle, left atrium or aorta of the patient;

accessing pediatric cardiology data;

utilizing the cardiology measurements for the patient and the pediatric cardiology data to calculate a current pediatric cardiology z-score for the patient; and displaying the current pediatric cardiology z-score and the one or more previously calculated pediatric cardiology z-scores for the patient together on the computerized graph, wherein the display indicates pediatric cardiology z-score trends.

12. The computer-readable storage media of claim 11, wherein the pediatric cardiology z-score is a measure of a distance of the patient's measurements in standard deviations of a sample from a mean.

13. The computer-readable storage media of claim 11, wherein the one or more previously calculated pediatric cardiology z-scores are the same type of z-score as the current pediatric cardiology z-score.

14. The computer-readable storage media of claim 11, wherein the current pediatric cardiology z-score displayed is directly associated with the cardiology measurements received.

15. The computer-readable storage media of claim 11, wherein the current pediatric cardiology z-score displayed is indirectly associated with the cardiology measurements received.

16. The computer-readable storage media of claim 11, wherein the pediatric cardiology data comprises one or more of pediatric cardiology z-score graph definitions, reference curves and data, and z-scores and measurements for previously treated patients.

17. The computer-readable storage media of claim 11, wherein the computerized graph is appropriate for the patient based on one or more of the patient's age, gender and ethnicity.

18. Computer-readable storage media having embodied thereon computer-useable instructions that, when executed, implement a method in a computerized health care environment for simultaneously displaying a documentation form for the entry of cardiology measurements and pediatric cardiology z-scores, the method comprising:

accessing one or more previously calculated pediatric cardiology z-scores for a patient from an electronic medical record source;

displaying the one or more previously calculated pediatric cardiology z-scores on a computerized graph; and displaying a documentation form for entry of one or more cardiology measurements for the patient simultaneously with the one or more previously calculated pediatric cardiology z-scores on the computerized graph, the one or more cardiology measurements comprising measurements associated with at least one of the left ventricle, right ventricle, left atrium or aorta of the patient, wherein the one or more cardiology measurements are utilized to calculate a current pediatric cardiology z-score for the patient; and displaying the current pediatric cardiology z-score for the patient on the computerized graph.

19. The computer-readable storage media of claim 18, wherein the previously calculated pediatric cardiology z-score is a measure of a distance of cardiology measurements of the patient in standard deviations of a sample from a mean.

20. A user interface embodied on at least one computer-readable storage medium, the user interface simultaneously displaying a documentation form for a pediatric cardiology patient and calculated z-scores, the interface comprising:

a first display area configured to display a documentation form for the pediatric cardiology patient, the documentation form for input of pediatric cardiology measurements for the patient, the pediatric cardiology measurements comprising measurements associated with at least one of the left ventricle, right ventricle, left atrium, or aorta of the pediatric cardiology patient; and a second display area configured to display a graph comprising one or more previously calculated pediatric cardiology z-scores for the pediatric cardiology patient and one or more currently calculated pediatric cardiology z-scores calculated utilizing the pediatric cardiology measurements for the patient.

* * * * *